United States Patent
Reed et al.

(10) Patent No.: US 9,507,486 B1
(45) Date of Patent: Nov. 29, 2016

(54) CONTEXT SWITCHING SYSTEM AND METHOD

(71) Applicant: ALLSCRIPTS SOFTWARE, LLC, Chicago, IL (US)

(72) Inventors: Christy Jill Reed, Raleigh, NC (US); Anthony Stuart, Wake Forest, NC (US)

(73) Assignee: ALLSCRIPTS SOFTWARE, LLC, Chicago, IL (US)

( * ) Notice: Subject to any disclaimer, the term of this patent is extended or adjusted under 35 U.S.C. 154(b) by 425 days.

(21) Appl. No.: 13/831,283

(22) Filed: Mar. 14, 2013

Related U.S. Application Data

(63) Continuation of application No. 13/732,110, filed on Dec. 31, 2012, now abandoned.

(60) Provisional application No. 61/692,703, filed on Aug. 23, 2012.

(51) Int. Cl.
*G06F 3/048* (2013.01)
*G06F 3/0481* (2013.01)

(52) U.S. Cl.
CPC .................... *G06F 3/0481* (2013.01)

(58) Field of Classification Search
CPC .......................... G06F 17/30997; G06F 3/012
USPC ........................................................ 715/781
See application file for complete search history.

(56) References Cited

U.S. PATENT DOCUMENTS

| 2010/0262928 | A1* | 10/2010 | Abbott | G06F 3/04817 715/769 |
| 2012/0023462 | A1* | 1/2012 | Rosing et al. | 715/863 |
| 2013/0185642 | A1* | 7/2013 | Gammons | 715/733 |
| 2013/0254705 | A1* | 9/2013 | Mooring | G06F 3/0488 715/784 |

* cited by examiner

*Primary Examiner* — William Bashore
*Assistant Examiner* — Rayeez Chowdhury
(74) *Attorney, Agent, or Firm* — Tillman Wright, PLLC; Chad D. Tillman; Jeremy C. Doerre

(57) ABSTRACT

A mobile computing device includes computer-executable instructions contained in nonvolatile computer-readable memory which, when executed by a processor of the device, perform a method including the steps of providing a plurality of application user interface screens, and enabling the person to navigate between the application user interface screens based on receiving user input by the person. Each application user interface screen represents a different context of use of the application for accomplishing a different respective result or performing a different respective activity by a person interacting with the application on the computing device. In variations thereof for use on PCs, application user interface windows are provided. In other variations, different user roles with different access privileges and/or different functionality forms the basis of the different contexts. I still other variations, both types of contextual bases are utilized.

18 Claims, 12 Drawing Sheets

CONTEXT SWITCHING SYSTEM AND METHOD

CROSS-REFERENCE TO RELATED APPLICATION

The present application is a U.S. continuation patent application of, and claims priority under 35 U.S.C. §120 to, U.S. non-provisional patent application Ser. No. 13/732,110, filed Dec. 31, 2012, which '110 patent application is hereby incorporated by reference herein, and which '110 application is a U.S. nonprovisional patent application of, and claims priority under 35 U.S.C. §119(e) to, U.S. provisional patent application Ser. No. 61/692,703, filed Aug. 23, 2012; and the present application is a U.S. nonprovisional patent application of, and claims priority under 35 U.S.C. §119(e) to, U.S. provisional patent application Ser. No. 61/692,703, filed Aug. 23, 2012, which '703 application is incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates user interfaces and, in particular, to user interfaces of a software application for display on a touchscreen, and preferably a touchscreen of a mobile device such as an iPad.

Determining feature sets of a software application can be challenging. Making applications that are visually clean and functionally intuitive often means streamlining functionality and offering basic or otherwise limited feature sets. An application that is focused on accomplishing a particular result or performing a particular activity and designed with just features used to accomplish such result or perform such activity can be quick and easy to learn and use.

Applications for use in a mobile environment are a good example of this. An application designed for use in mobile environments typically is installed and used with other related applications, all of which can even be bundled together, with each application being a plugin or otherwise a narrowly focused application for accomplishing a particular result or performing a particular activity. This approach avoids the single monolithic application. Moreover, this practice is facilitated by the easy distribution of apps through 'app stores' making the delivery of targeted apps for specific workflows much more efficient for software vendors. Nevertheless, this benefit to overall application design leads to the detriment of the overall user experience, as the user will often need to close a current application and open a new one in order to accomplish the different result or perform the different activity using the other application.

At the other extreme, an application that accomplishes all of the goals conventionally is cluttered with features and typically is not visually streamlined, clean, or intuitive. In such monolithic applications, the categorization of features and functions are broken into submenus or buried hierarchies within a single, overarching, user interface. This often leads to incredibly complex software programs that don't provide users with intuitive ways of accomplishing tasks.

Nonetheless, such monolithic applications persist because applications that have many different feature sets collectively fulfilling many different use cases can have a broad and diverse market appeal to a large client base, and thus can be attractive to vendors. For these reasons, an application that may start out as a targeted application to a subset of clients also may evolve over the years toward a 'one-size-fits-all' application. As applications progress through their lifecycles, such feature creep can lead to extremely cluttered screens, making even the simplest of tasks more frustrating to perform.

An intended benefit of one or more aspects and features of the invention is the provision of an application that accomplishes a multitude of such disparate results or performs such disparate functions, which application is visually clean and functionally intuitive, wherein the application includes a plurality of different user interfaces each one being designed within the context of a respective particular result to be achieved or activity to be performed.

Additionally, an application may provide for different user roles, each user role having different access and use privileges. Moreover, the same person may have the ability to log into the application as one of a plurality of user roles; however, the person conventionally logs out of the application under one user role before the same person can log into the application under the other user role. In any event, the person generally must log in under a selected user role in order for that person to interact with the application within the context of the selected user role.

Another intended benefit of one or more aspects and features of the invention is the provision of an application that does not require a person to log out under one user role and then log back in under another user role for purposes of changing the context within which the person interacts with the application.

SUMMARY OF THE INVENTION

The present invention includes many aspects and features. Moreover, while many aspects and features may be described with respect to healthcare, the present invention is not limited to use only in healthcare, as will become apparent from the following summaries and detailed descriptions of aspects, features, and one or more embodiments of the present invention. Indeed, the user interfaces and user interface methodologies are generally as applicable in healthcare as in other industries outside of healthcare.

Accordingly, an aspect of the present invention relates to a computing device including a processor for executing computer-executable instructions performing a method. The method comprises the steps of providing a plurality of application user interface screens of an application, each application user interface screen including a different context of use of the application, and enabling a user to navigate between the plurality of application user interface screens based on receiving a predefined input by the user.

In a feature of this aspect, the method further comprises detecting an input from the user, and determining if the detected input from the user is the predefined input.

In a variation of this feature, the plurality of application user interface screens are arranged in a navigational sequence.

In a variation of this feature, the method further comprises displaying to the user a next application user interface in the plurality of application user interfaces in the navigational sequence when the predefined input is detected.

In a variation of this feature, the navigational sequence is arranged along an axis.

In a variation of this feature, the predefined input is based at least on the navigational sequence.

In a variation of this feature, the navigational sequence is arranged along a horizontal axis.

In a variation of this feature, the predefined input is horizontal gesture by the user.

In a variation of this feature, the computing device includes a touchscreen.

In a variation of this feature, the horizontal gesture includes swiping the user's two fingers to the left or right along the touchscreen.

In a variation of this feature, the navigational sequence is arranged along a vertical axis.

In a variation of this feature, the predefined input is a vertical gesture by the user.

In a variation of this feature, the computing device includes a touchscreen.

In a variation of this feature, the vertical gesture includes swiping the user's two fingers up or down along the touchscreen.

In a feature of this aspect, the navigational sequence is a wheel, such that a first application user interface screen is displayed after a last application user interface screen when the predefined input is detected.

In a variation of this feature, each of the different contexts accomplish different results or perform a particular activity.

In a variation of this feature, the plurality of application user interface screens includes a first subset of application user interface screens and a second subset of application user interface screens.

In a variation of this feature, a first navigational sequence of the first subset of application user interface screens is arranged along a horizontal axis, and a second navigational sequence of the second subset of application user interface screens is arranged along a vertical axis.

In a variation of this feature, a first predefined input of the first navigational sequence is a horizontal gesture by the user, and a second predefined input of the first navigational sequence is a vertical gesture by the user.

In a variation of this feature, the computing device includes a touchscreen.

In a variation of this feature, the horizontal gesture includes swiping the user's two fingers to the left or right along the touchscreen, and the vertical gesture includes swiping the user's two fingers up or down along the touchscreen.

In a feature of this aspect, the method further comprises determining a current navigational sequence being used by the user, and determining if the detected predefined input from the user is the first predefined input or the second predefined input.

In a variation of this feature, the method further comprising if the current navigational sequence is the first navigational sequence, displaying a next application user interface screen in the first subset of application user interface screens when the determined predefined input from the user is the first predefined input, and if the current navigational sequence is the second navigational sequence, displaying a next application user interface screen in the second subset of application user interface screens when the determined predefined input from the user is the second predefined input.

In a variation of this feature, wherein at least one of the application user interface screens in the first subset of application user interface screens is included in the second subset of application user screens.

In a variation of this feature, the method further comprising if the application user interface being displayed is the application user interface screen included in the first and second subsets of application user interface screens, displaying a next application user interface screen in the first subset of application user interface screens when the determined predefined input from the user is the first predefined input, or displaying a next application user interface screen in the second subset of application user interface screens when the determined predefined input from the user is the second predefined input.

In a variation of this feature, wherein the computing device includes a mouse.

In a variation of this feature, wherein the horizontal gesture includes moving the mouse horizontally to the left or right, and the vertical gesture includes moving the mouse vertically up or down.

In a variation of this feature, the method further comprising determining a current navigational sequence being used by the user, and determining if the detected predefined input from the user is the first predefined input or the second predefined input.

In a variation of this feature, the method further comprising if the current navigational sequence is the first navigational sequence, displaying a next application user interface screen in the first subset of application user interface screens when the determined predefined input from the user is the first predefined input, and if the current navigational sequence is the second navigational sequence, displaying a next application user interface screen in the second subset of application user interface screens when the determined predefined input from the user is the second predefined input.

In a variation of this feature, wherein at least one of the application user interface screens in the first subset of application user interface screens is included in the second subset of application user screens.

In a variation of this feature, the method further comprising if the application user interface being displayed is the application user interface screen included in the first and second subsets of application user interface screens, displaying a next application user interface screen in the first subset of application user interface screens when the determined predefined input from the user is the first predefined input, or displaying a next application user interface screen in the second subset of application user interface screens when the determined predefined input from the user is the second predefined input.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Figure 1:
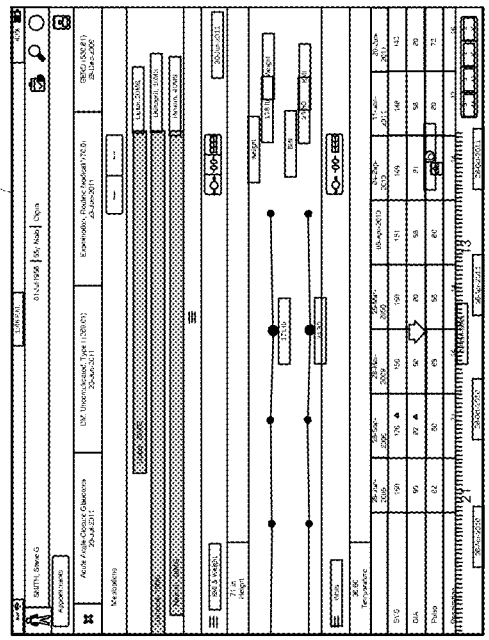
FIG. 1 illustrates navigation between two application user interface screens of an application, each application user interface screen having the same skin.
Figure 1:
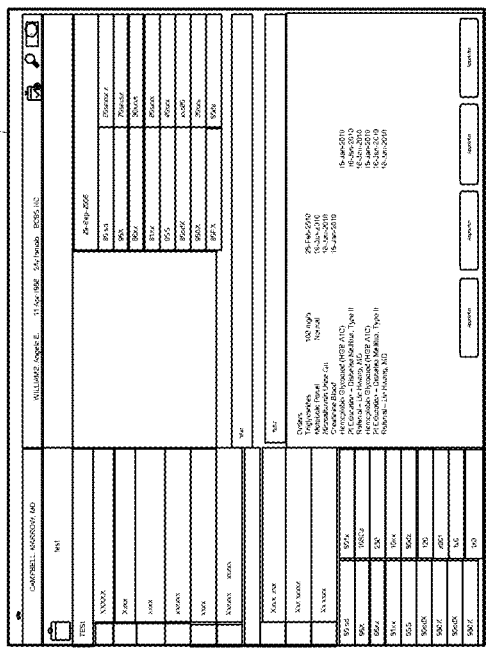

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself. Nor is any intended benefit of an aspect or feature of the invention intended to be a limitation of any particular claim unless explicitly set forth in such claim.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

Turning now to the figures, one or more preferred embodiments are described with regard to implementation on a mobile computing device comprising a tablet, such as an iPad. With reference to a tablet, a plurality of "application user interface screens" preferably are provided by an application. Each such application screen preferably consumes the display of the tablet when active and focus is not switched to something else such as, for example, a multi-tasking bar found in iOS 5. In contrast, when used in connection with a PC, such as a laptop or desktop computer, a plurality of "application user interface windows" preferably are provided by an application.

FIG. 1 illustrates navigation between two application user interface screens 102,104. Each of the application user interface screens 102,104 is illustrated as having a common theme or skin. Additionally, the navigation is illustrated as being horizontal by way of, for example, a horizontal two-finger swipe on the touchscreen of a tablet. Preferably, such navigation is achieved by a person's hand gesture on a touchscreen of the tablet. The hand gesture may comprise a two-finger swipe. Alternatively, the gesture may comprise a three or four figure swipe, or a circular or arching motion, or some other defined motion. The defined motion further may be dependent on direction and/or orientation, such as leftto-right swiping, right-to-left swiping, diagonal swiping, vertical swiping, and horizontal swiping.

Each of the application user interface screens 102,104 of FIG. 1 is provided by an application, and the functions provided in each respective application user interface screen 102,104 are preferably designed toward accomplishing a particular result or performing a particular activity. In this respect, when different results or activities within a single application form the bases of different contexts (i.e., context of use in this example), then the options and functionality presented for selection by the person will be logically grouped with respect to such contexts with the appropriate group being included in the respective application user interface screen, and the person can scroll between the application user interface screens using the predefined user input, such as two-finger horizontal swiping, for example.

In an exemplary healthcare implementation, application user interface screen 104 comprises a "patient view" in which vitals and other healthcare information of patient is presented for review by a healthcare professional before, during, and/or after a visit with the patient. The features and functionality included within the patient view application user interface screen is designed to support, enable, and otherwise facilitate the patient visit. In contrast, the application user interface screen 102 comprises a "task view", where the same person is able to perform general office tasks like attending to email, calendar, and task management.

In accordance with the disclosed method, the healthcare professional is therefore able to navigate between the patient view 104 and the task view 102 using the predefined user input, e.g., two-finger horizontal swipe, without opening and closing a new application. As indicated, each context included in the application may be accessed by performing the predefined input. Although two application user interface screens have been illustrated, the disclosed system and method are not limited to two.

Figure 2:
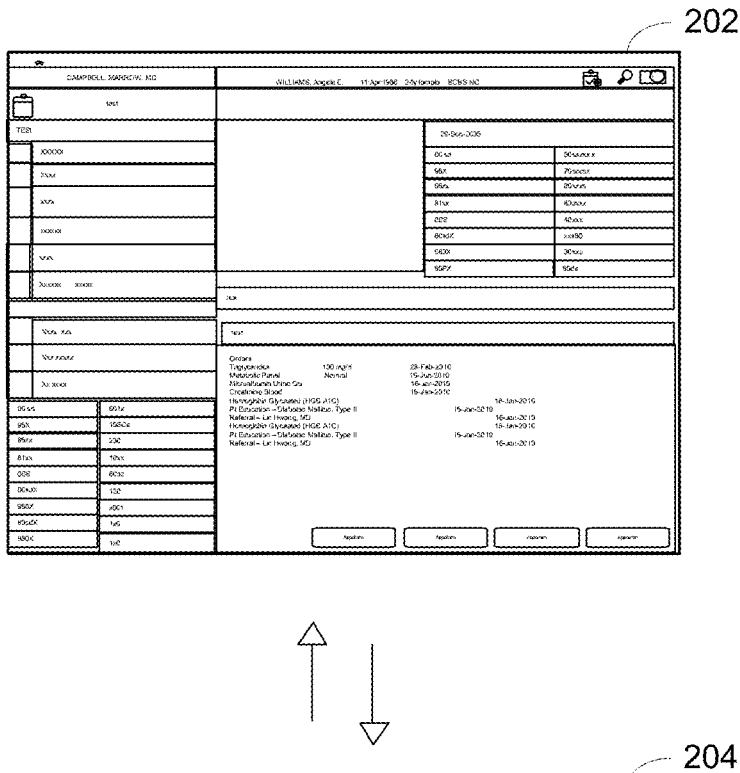
FIG. 2 illustrates navigation between two application user interface screens of an application, each application user interface screen having a different skin.
Figure 2:
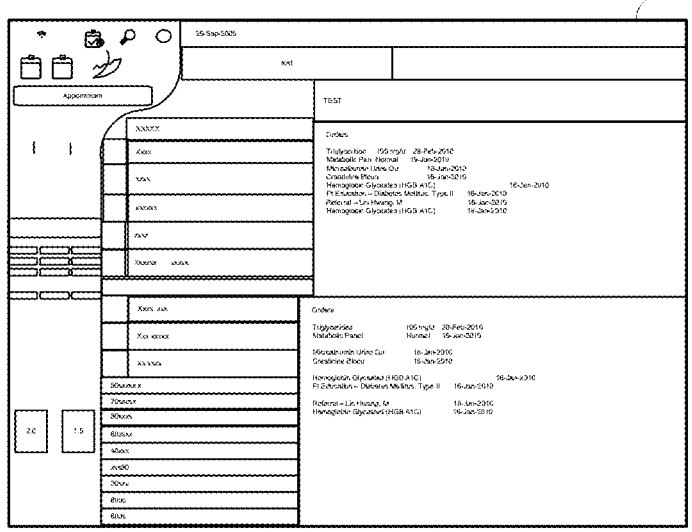

Each application user interface screen may be linked along a virtual "axis". As illustrated in FIG. 1, the application user interface screens 102,104 are linked along the virtual horizontal axis. In FIG. 2, the application user interface screens are linked along the virtual vertical axis, to be disclosed hereinafter. The virtual axis is at least one of the elements that determines the predefined user input required to navigate between multiple application user interface screens. As disclosed above, in order for a user to navigate between the patient view 104, illustrated in FIG. 1, to the task view 102, the user must perform a two-finger horizontal swipe. The link between the patient view 10 and the task view 102 in along the virtual horizontal axis, in the FIG. 1 example.

Figure 10:
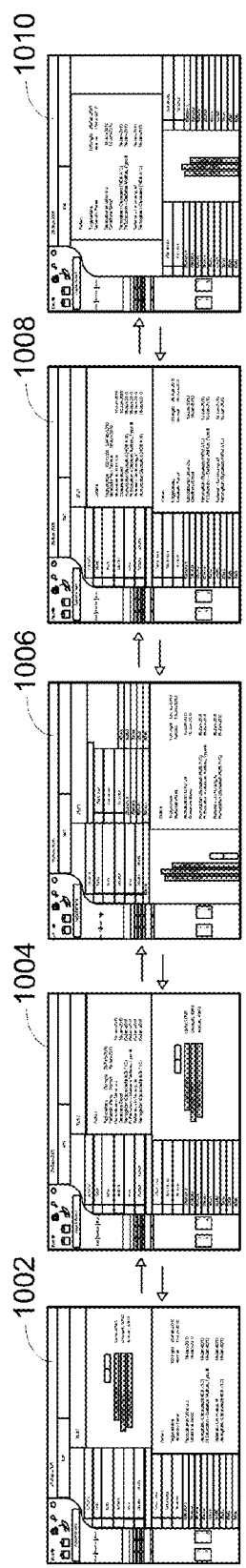
FIG. 10 illustrates navigation between a plurality of application user interface screens.

Another example of the disclosed method and system is illustrated in FIG. 10. As shown, an application includes a plurality of application user interface screens 402 . . . 410. As exemplified in FIG. 10, each of the application user interface screens 1002 . . . 1010 are linked along the virtual horizontal axis, and may be navigated through using a single predefined input, for example a two-finger horizontal swiping.

FIG. 2 illustrates an example vertical navigation between two application user interface screens 202,204. Each of the application user interface screens 202,204 may have a different theme or skin and are linked along the virtual vertical axis. Accordingly, navigating between the application user interface screens 202,204 may include a predefined input in the vertical direction, for example, a two-finger vertical swipe.

In an alternative implementation of the disclosed system and method, the virtual axis alng which the plurality of application user interface screens are linked may also indicate the type of user authorized to navigate between the application user interface screens. Referring back to FIG. 2, in accordance with this disclosed implementation, the application user interface screen 202 may be for use by a user within the user role of an administrator, for example. The application user interface screen 204 may be for use by the same person within the user role of a regular user, for example. The user, therefore, may switch user roles within the same application (i.e., changes contexts) by performing a predefined input, for example, the vertical two-finger swipe.

In accordance with this implementation, a user preferably enters and saves different login credentials for each user role when setting up the application. Thereafter, upon logging in with either credentials under a particular user role, the user may switch between his or her user roles by providing the pre-defined input, e.g., two-finger hand swipe or other predefined gesture. The requirement for the user to log out and then log back in using the credentials for the other user role is eliminated.

Figure 4:
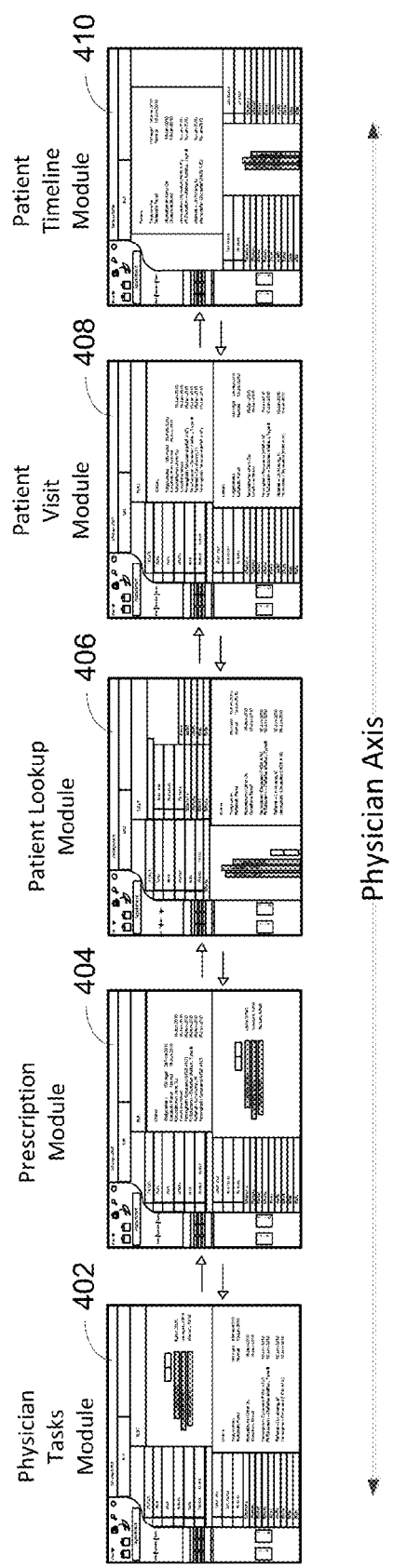
FIGS. 4 and 4a illustrates a plurality of application user interface screens along a common navigational axis.

FIG. 4 illustrates a plurality of application user interface screens along a common navigational axis. As illustrated, the application user interface screens 402 . . . 410 are intended for use by a person logged in as a physician and, accordingly, the axis is labeled the physician axis in FIG. 4. Further as illustrated, navigation is linear along the axis.

Figure 4A:
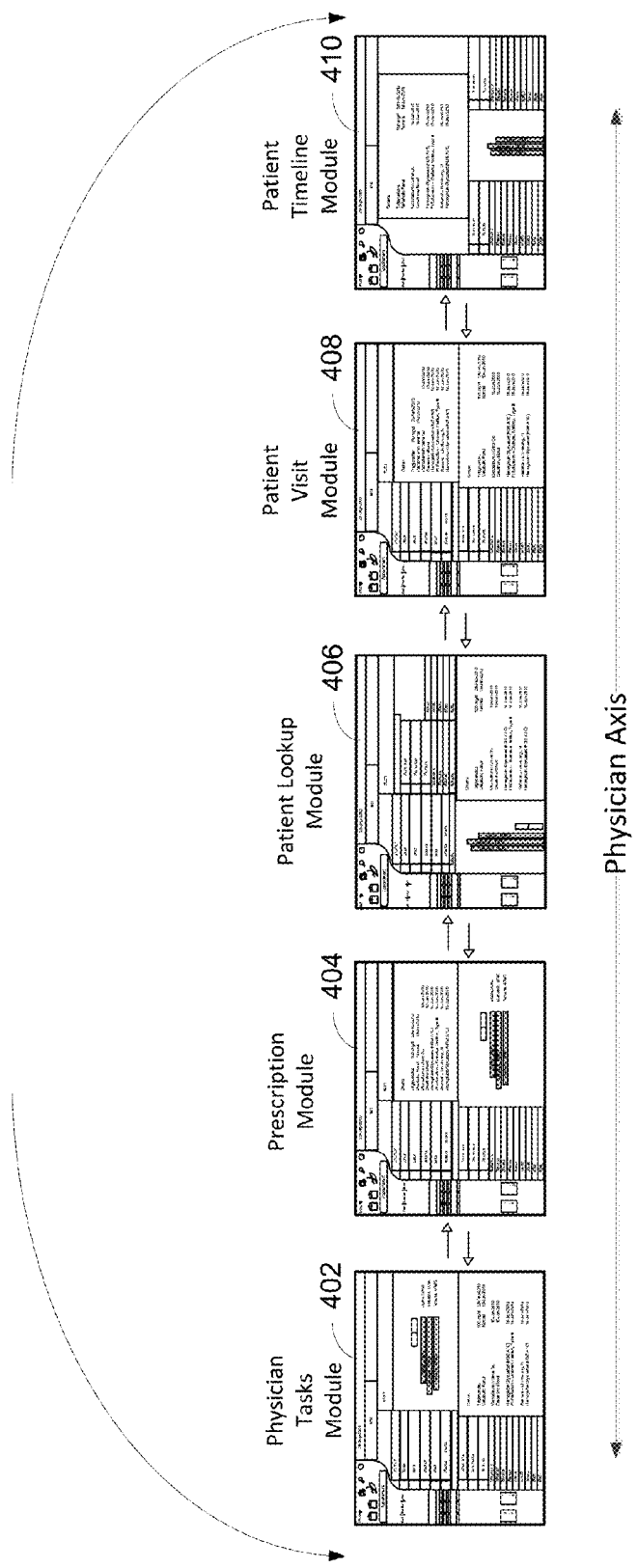

FIG. 4a represents a variation of the application user, wherein navigation is circular and resembles a carousel application user interface screens 402 . . . 410 of FIG. 4. The context basis illustrated in FIG. 4 though is still used.

Figure 5:
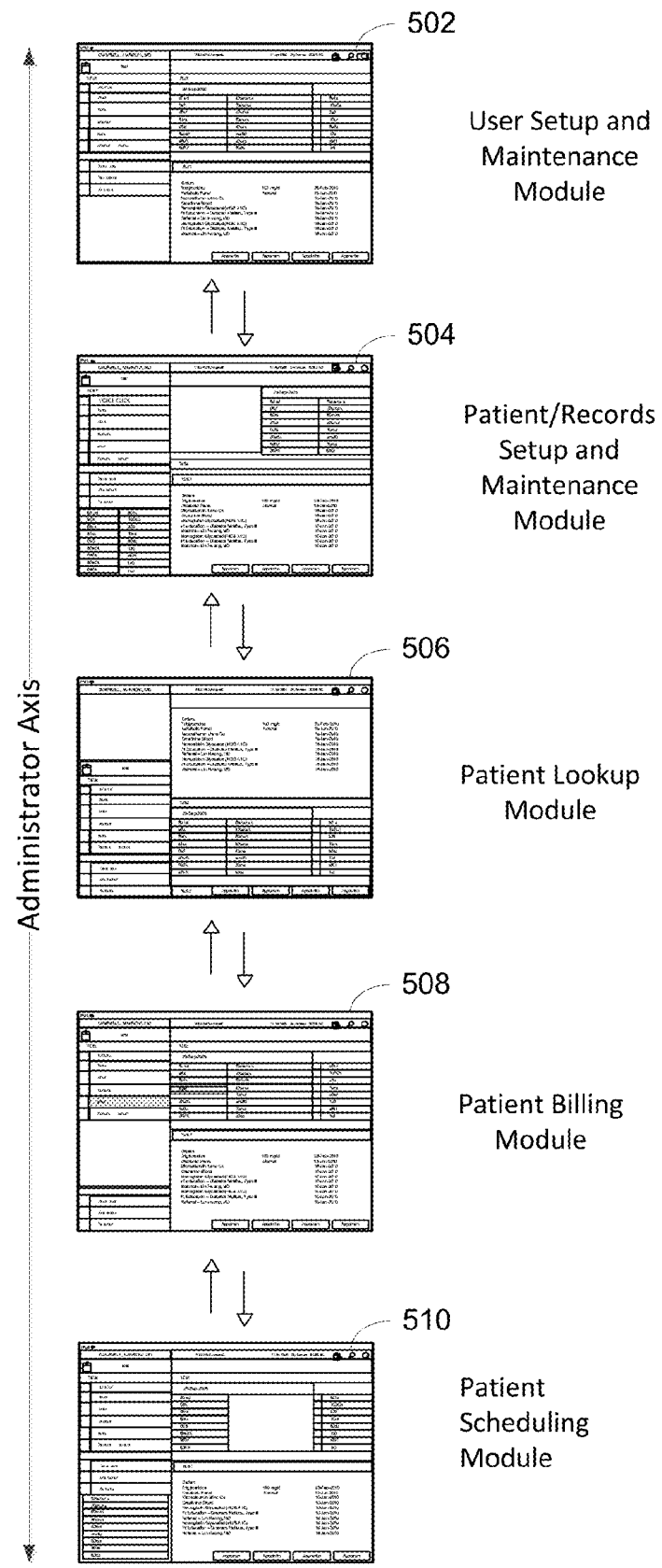
FIGS. 5 and 5a illustrates a plurality of application user interface screens along a common navigational axis.
Figure 5A:
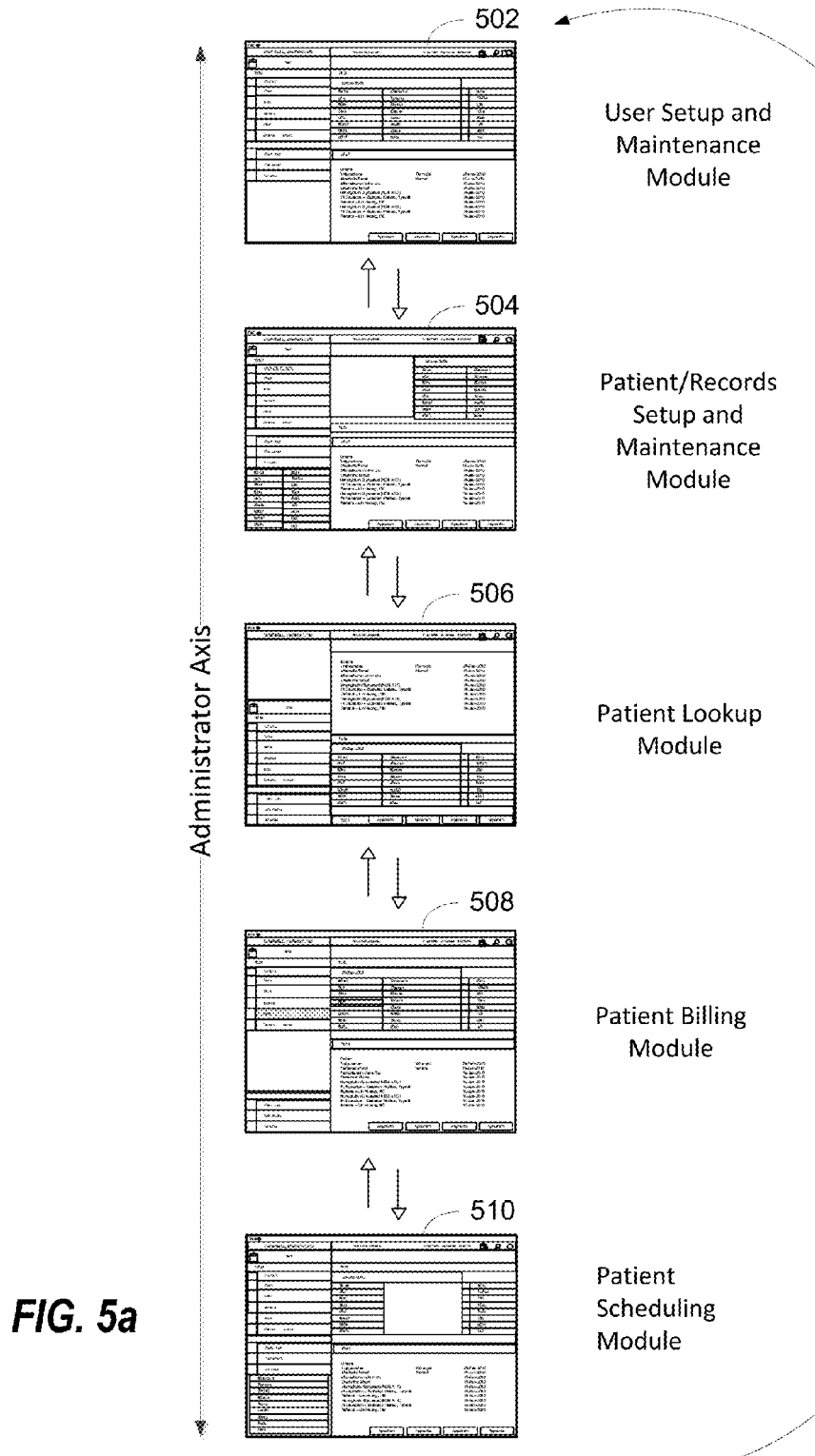

FIG. 5 illustrates an example of a plurality of application user interface screens 502 . . . 510 along a common navigational axis. As illustrated, the application user interface screens 502 . . . 510 are intended for use by a person logged in as an administrator and, accordingly, the axis is labeled the administrator axis. Further as illustrated, navigation is linear along the axis. FIG. 5a represents an example variation of the application user interface screen navigation illustrated in FIG. 5, wherein in which navigation is circular and resembles a carousel. The context basis, though, of the application user interface screens 502 . . . 510 of FIG. 5 remains the same.

Figure 3:
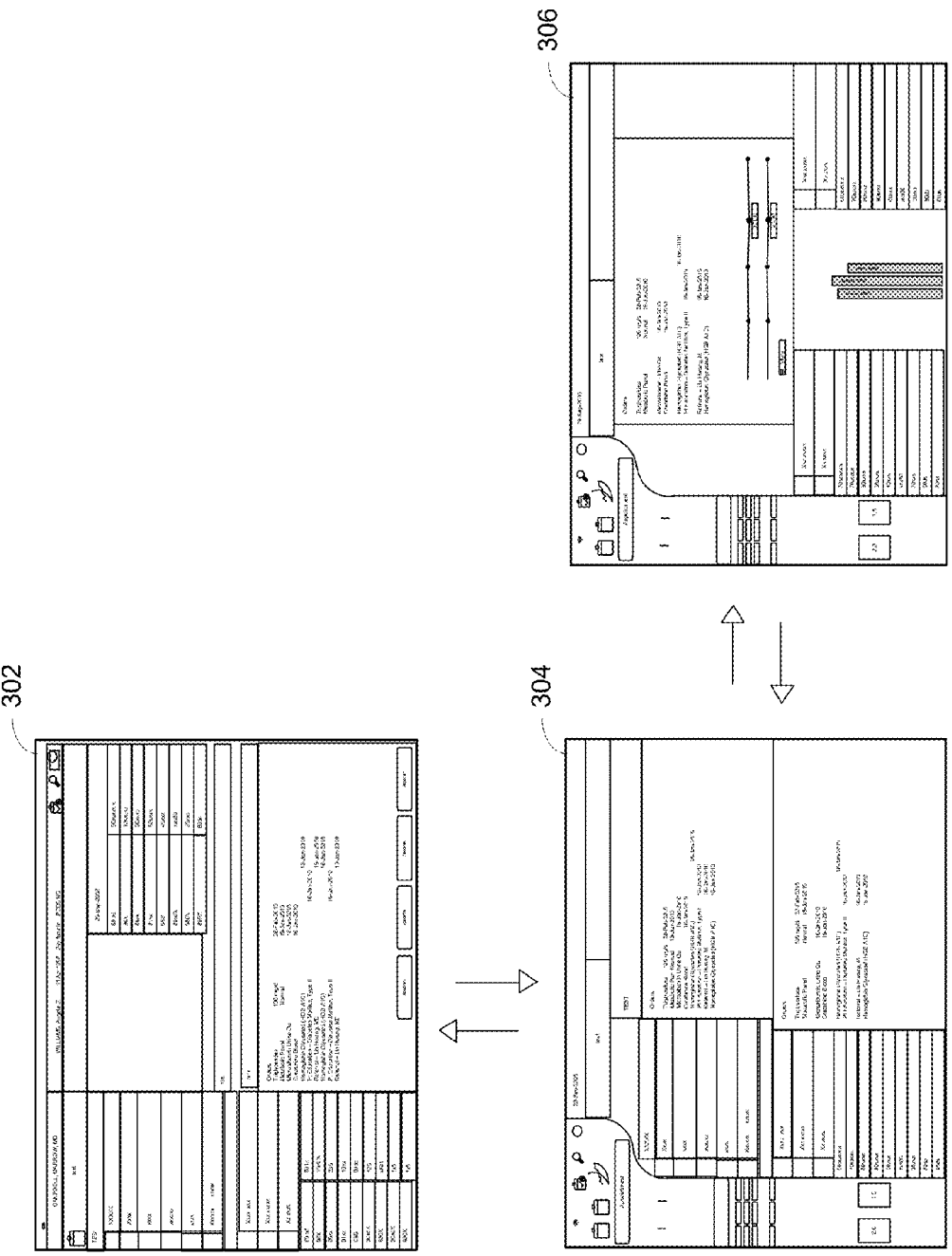
FIG. 3 illustrates navigation between three application user interface screens.

FIG. 3 illustrates navigation between three application user interface screens 302,304,306. As disclosed above, the application user interface screens 302,304,306 may be limited along a virtual axis. As exemplified in FIG. 3, application user interface screens 304 and 306 are linked along the virtual horizontal axis, and application user interface screens 304 and 302 are linked along the virtual vertical axis. In accordance with the disclosed implementation, the application user interface screens 304 and 306 may have the same theme or skin, such that as the user navigates between the application user interface screens 304,306, the user is virtually aware that although the screen has changed, the theme or user mode remains the same.

Application user interface screens 302,304, as illustrated, do not have the same theme or user mode. Application user interface screen 304 allows the user to navigate between themes or user modes using the predefined input, for example, the two-finger vertical swipe. In one example, application user interface screen 302 may be a task view requiring the user to be in the admin user mode. Applicant user interface screen 304 may be a patient view, requiring the user to be logged in the physician mode. The disclosed system and method, therefore, allow the user to navigate between application user interface screens 304, 306 in the physician user mode by performing the predefined input, e.g., the two-finger horizontal swipe, and then, from screen 304, operating in the task view 302 in the admin user mode by performing the predefined input, e.g., the two-finger swipe.

Figure 6:
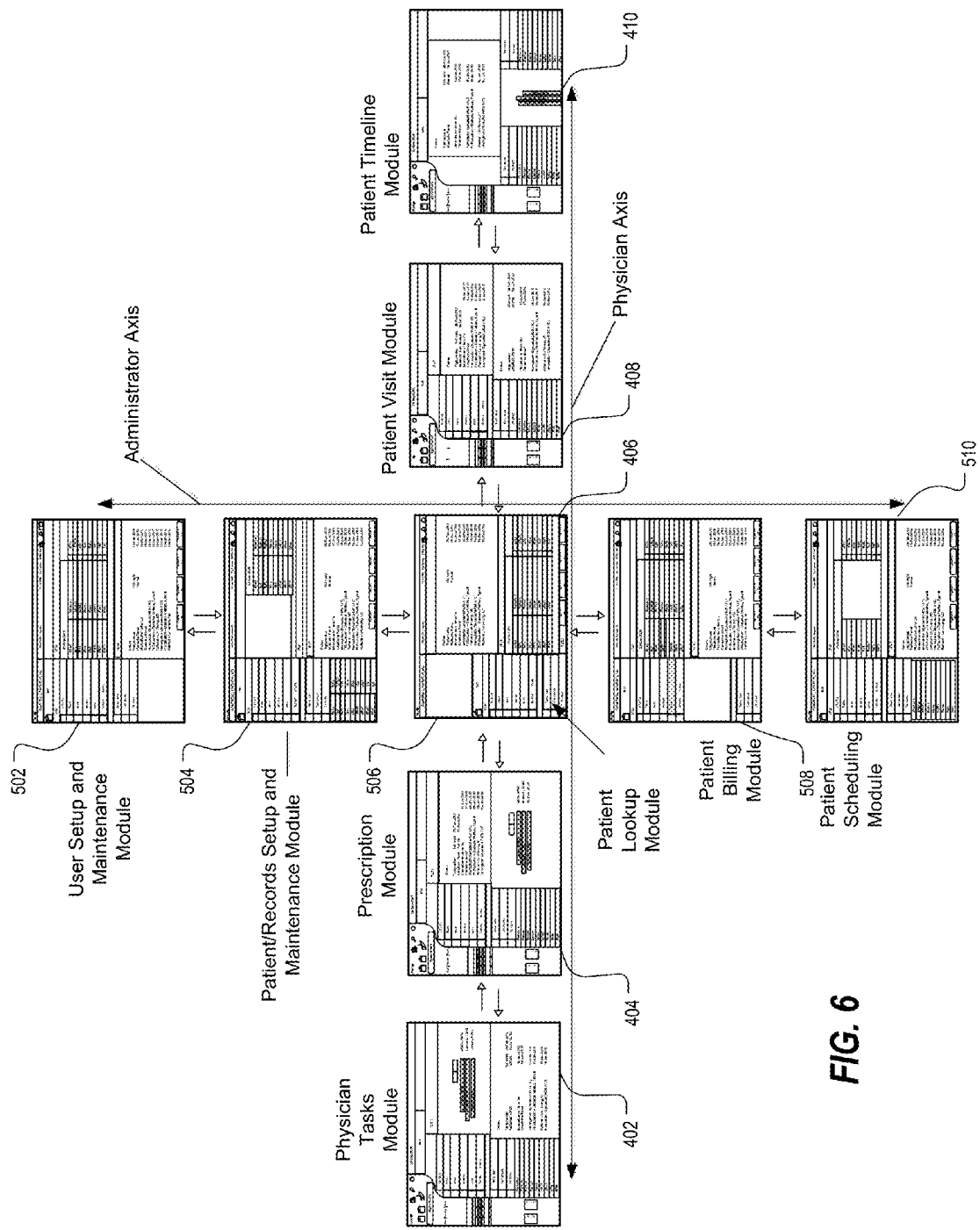
FIGS. 6 and 7 each illustrates the combination of the physician axis and the administrator axis, which may arise when the same person using the illustrated application has both physician and administrator credentials.
Figure 7:
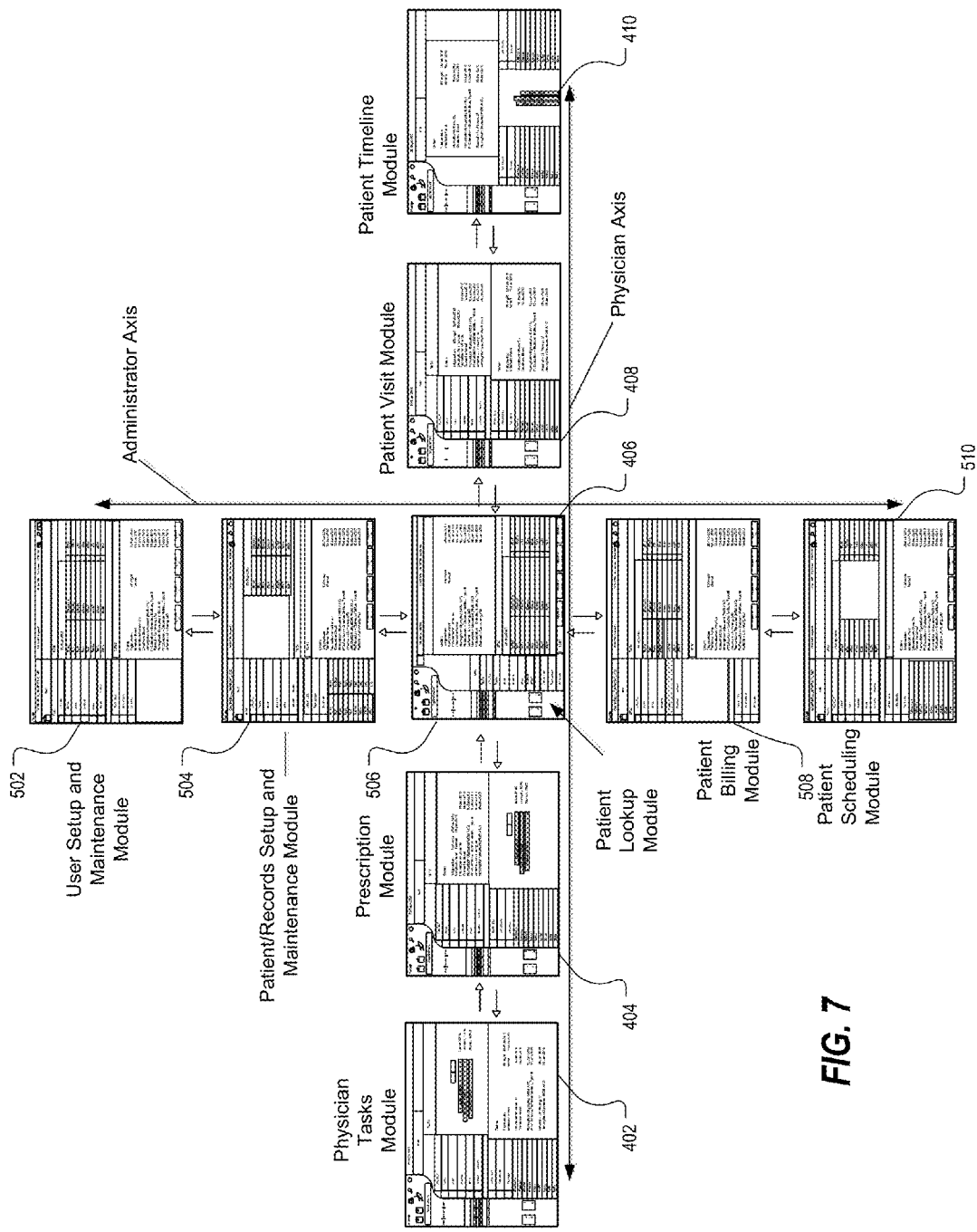

FIGS. 6 and 7 each illustrate example user combinations of the physician axis and the administrator axis illustrated in FIGS. 4, 4*a*, 5, and 5*a*, which may arise when the same person using the illustrated application has both physician and administrator credentials. Further in this respect, it will be appreciated that application user interface screens 406 and 506 are both patient lookup modules and that the same application user interface screen may be shared between both the physician axis and the administrator axis. Furthermore, the skin for the application user interface screen corresponds to the skin of the axis along which navigation was last performed.

Thus, in FIG. 6, the application user interface screen 506 for the patient lookup module is shown with the skin for the administrator axis, indicating that navigation last occurred along the administrator axis; in FIG. 7, the application user interface screen 406 for the patient lookup module is shown with the skin for the physician axis, indicating that navigation last occurred along the physician axis. In this way, a user performing a patient lookup at the application user interface screen 406,506 will know, based on the skin, the current user role within which the user is interacting with the application. Accordingly, for the example illustrated in FIG. 7, the current user role is physician.

Figure 8:
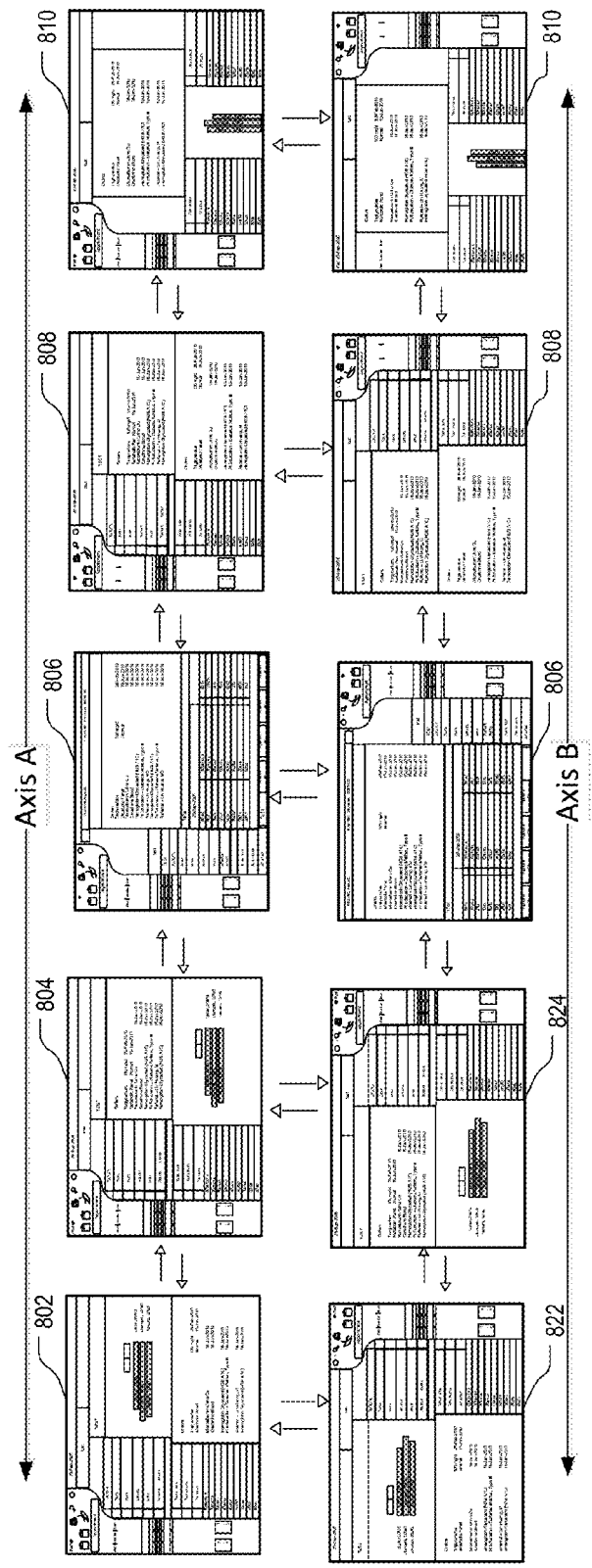
FIG. 8 illustrates two navigational axis A,B that extend in parallel to each other.

Two navigational axis A,B that extend in parallel to each other are illustrated in FIG. 8. The application user interface screens 802 . . . 810 along Axis A have different contexts based on use; the application user interface screens 822 . . . 830 along Axis B have different contexts based on use; and the application user interface screens 802 . . . 810 of Axis A have different contexts based on user roles from the application user interface screens 822 . . . 830 of Axis B. Moreover, at each application user interface screen 802 . . . 810 and 822 . . . 830, the user is able to navigate between the two different user roles quickly and efficiently.

Figure 9:
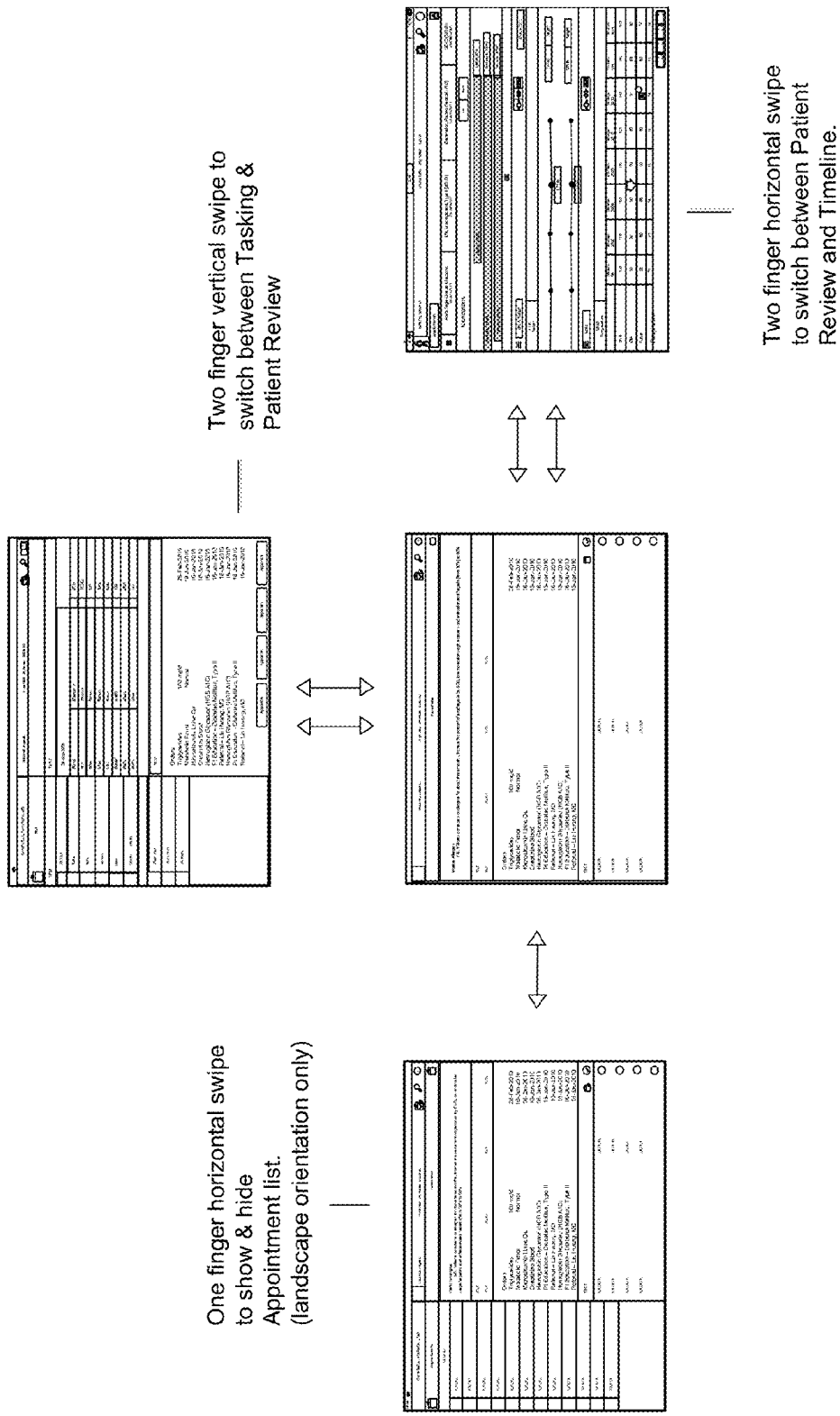
FIG. 9 illustrates a screenshot of a help module of a commercial app for an iPad, wherein one or more aspects and features of the present invention are described for use by a person.

In addition to the foregoing, FIG. 9 illustrates a screenshot of a help module of a commercial app for an iPad, wherein one or more aspects and features of the present invention are described for use by a person.

It will be appreciated from the foregoing that, in accordance with one or more aspects and features of the present invention, a method for context switching within a single software application is provided that allows for greater overall situational awareness by a person interacting with the application; that includes the addition of context-specific features and functions without visually cluttering application; and that provides multiple efficiencies related to the development, maintenance, and distribution of an application.

Multiple commercial advantages are believed to be provided by one or more aspects and features of the present invention. These advantages extend to any industry or commercial implementation and are not limited to a healthcare setting. Indeed, it is believed that one or more aspects and feature of the present invention can be used in just about any software application having a sufficient degree of complexity or excessive features/functions that can be categorized into different work-related flows for accomplishing respective results or performing respective activities.

In addition, as will be understood from the foregoing, there are two different groups that may benefit: the persons who use the applications, and the vendors which provide and maintain the applications. For the user, the splitting of the software into logical silos streamlines the interaction of the person with any particular for achieving a particular result or performing a particular activity. This creates a hierarchy that is much more "flat" than a hierarchy of like functions in a single monolithic user interface, which is believed to offer a more intuitive and user friendly experience. Such a flat hierarchy can potentially lead to dramatic decreases in task time, the time required for way-finding and fact-finding, and overall lower levels of mental/cognitive workload through the reduction of visual clutter and a reduced tax on the working memory of the user.

From a vendor perspective, benefit arises from increased sales that often accompany easier-to-use software (ease of use is believed to be an extremely valuable SW differentiator). Additional vendor advantages includes efficiencies in software development expense arising from more functions being provided in less products without sacrificing usability, less overhead in sales distribution than would be incurred for an expanded product line, and overall financial benefits of a simplified product portfolio.

Furthermore, by keeping the user in a single application interface instead of shifting between many related, targeted applications, the overall issues surrounding "flow" and situational awareness are mitigated. Also, by providing simple gestures for faster context switching, the current design reduces the load on a user's working memory system, as any "carry over" information that the user needs to keep in mind while switching contexts would no longer need to persist through the processing of closing one application, finding the launch, and the actual load time of the second, related application. Instead, a quick swipe takes the user to a logical landing point in the new context with a simple, intuitive action.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method executed by a processor included in a tablet device comprising the steps of:
   (a) providing a plurality of application user interface screens of a healthcare software application oriented along a horizontal axis, each application user interface screen oriented along the horizontal axis being associated with a different application context;
   (b) providing a plurality of application user interface screens of the application oriented along a vertical axis, each application user interface screen oriented along the vertical axis being associated with a different user role context;
   (c) enabling a user to navigate between the plurality of application user interface screens oriented along the horizontal axis based on receiving a first predefined input by the user; and
   (d) enabling the user to navigate between the plurality of application user interface screens oriented along the vertical axis based on receiving a second predefined input by the user.

2. The method of claim 1, wherein a first user interface screen oriented along the vertical axis is associated with a physician user role context, and a second user interface screen oriented along the vertical axis is associated with an administrator user role context.

3. A method executed by a processor included in a tablet device comprising the steps of:
   (a) providing a plurality of application user interface screens of a healthcare software application oriented along a horizontal axis, each application user interface screen oriented along the horizontal axis being associated with a different application context;
   (b) providing a plurality of application user interface screens of the application oriented along a vertical axis, each application user interface screen oriented along the vertical axis being associated with a different user role context;
   (c) enabling a user to navigate between the plurality of application user interface screens oriented along the horizontal axis based on receiving a first predefined input by the user and between the plurality of application user interface screens oriented along the vertical axis based on receiving a second predefined input by the user, such enabling including
      (i) displaying, to the user via a touchscreen of the tablet device, a first user interface screen of the application;
      (ii) receiving, from the user via the touchscreen, input corresponding to a first input swipe pattern;
      (iii) determining, utilizing one or more processors of the tablet device, whether the first input swipe pattern matches
         (A) a first predefined swipe pattern corresponding to a change in application context, or
         (B) a second predefined swipe pattern corresponding to a change in user role context;
      (iv) displaying, to the user via the touchscreen, a second user interface screen of an application selected based on the determination;
      (v) wherein the second user interface screen
         (A) has a different application context from the first user interface screen if the first input swipe pattern was determined to match the first predefined swipe pattern, or
         (B) has a different user role context from the first user interface screen if the first input swipe pattern was determined to match the second predefined swipe pattern.

4. The method of claim 3, wherein the first user interface screen has a physician user role context.

5. The method of claim 3, wherein the second user interface screen has an administrator user role context.

6. The method of claim 3, wherein the user is a health care practitioner.

7. The method of claim 3, wherein the user is a physician.

8. The method of claim 3, wherein the first predefined swipe pattern comprises a horizontal swipe.

9. The method of claim 3, wherein the first predefined swipe pattern comprises a vertical swipe.

10. The method of claim 3, wherein the first predefined swipe pattern comprises a two-finger horizontal swipe.

11. The method of claim 3, wherein the first predefined swipe pattern comprises a horizontal swipe and the second predefined swipe pattern comprises a vertical swipe.

12. The method of claim 3, wherein the first predefined swipe pattern comprises a two-fingered horizontal swipe and the second predefined swipe pattern comprises a two-fingered vertical swipe.

13. A method executed by a processor included in a tablet device comprising the steps of:
   (a) providing a plurality of application user interface screens of a healthcare software application oriented along a horizontal axis, each application user interface screen oriented along the horizontal axis being associated with a different application context;
   (b) providing a plurality of application user interface screens of the application oriented along a vertical axis, each application user interface screen oriented along the vertical axis being associated with a different user role context;
   (c) enabling a user to navigate between the plurality of application user interface screens oriented along the horizontal axis based on receiving a first predefined input by the user and between the plurality of application user interface screens oriented along the vertical axis based on receiving a second predefined input by the user, such enabling including
      (i) displaying, to a user via a touchscreen of the tablet device, a first user interface screen of the application;
      (ii) receiving, from the user via the touchscreen, input corresponding to a first input swipe pattern;
      (iii) determining, utilizing one or more processors of the tablet device, that the first input swipe pattern matches a first predefined swipe pattern corresponding to a change in application context;
      (iv) displaying, to the user via the touchscreen, a second user interface screen of an application selected based on the determination that the first input swipe pattern matches the first predefined swipe pattern, the second user interface screen having a different application context from the first user interface screen;

(v) receiving, from the user via the touchscreen, input corresponding to a second input swipe pattern;

(vi) determining, utilizing one or more processors of the tablet device, that the second input swipe pattern matches a second predefined swipe pattern corresponding to a change in user role context;

(vii) displaying, to the user via the touchscreen, a third user interface screen of an application selected based on the determination that the second input swipe pattern matches the second predefined swipe pattern, the third user interface screen having a different user role context than the first or second user interface screens.

14. The method of claim 13, wherein the first and second user interface screens have a physician user role context.

15. The method of claim 13, wherein the third user interface screen has an administrator user role context.

16. The method of claim 13, wherein the user is a health care practitioner.

17. The method of claim 13, wherein the first predefined swipe pattern comprises a two-finger horizontal swipe.

18. The method of claim 13, wherein the first predefined swipe pattern comprises a horizontal swipe and the second predefined swipe pattern comprises a vertical swipe.

* * * * *